United States Patent [19]

Simpson

[11] 4,174,202

[45] Nov. 13, 1979

[54] KIT AND METHOD FOR TESTING LIQUIDS FOR HYDROGEN SULFIDE CONTENT

[75] Inventor: Benny E. Simpson, Tulsa, Okla.

[73] Assignee: The Dow Chemical Company, Midland, Mich.

[21] Appl. No.: 855,540

[22] Filed: Nov. 28, 1977

[51] Int. Cl.$^2$ ............................................. G01N 31/22
[52] U.S. Cl. ............................... 23/230 R; 23/232 R; 422/56; 422/58; 422/61; 422/68
[58] Field of Search .......... 23/230 R, 253 TP, 254 R, 23/232 R, 253 R, 259

[56] References Cited

U.S. PATENT DOCUMENTS

| 2,864,725 | 12/1958 | Sorg et al. | 23/230 R X |
| 3,528,775 | 9/1970 | O'Hara et al. | 23/230 HC |

OTHER PUBLICATIONS

Aloe Scientific Catalog 103, pp. 157, 1010, 1048.
Hach Catalog 11A, p. 27.

Primary Examiner—Joseph Scovronek
Assistant Examiner—Arnold Turk
Attorney, Agent, or Firm—Glenn H. Korfhage

[57] ABSTRACT

A method for quickly determining whether or not the $H_2S$ concentration in fluids exceeds a preselected level, such as that set by government standards for oil field fluids, comprises: (1) admixing a preselected quantity of a liquid to be tested with a quantity of metal ion (such as $Cd^{++}$) capable of reacting with sulfide ion to form a precipitate, the quantity of metal ion being equal to that required to precipitate a preselected amount of sulfide ion; (2) purging any residual $H_2S$ from the liquid (such as by generating $CO_2$ in situ); (3) contacting a reagent colorimetrically and selectively responsive to the presence of $H_2S$ (such as lead acetate) with gas purged from the liquid; and (4) observing the color of colorimetrically responsive reagent.

A kit convenient for use in carrying out the method in the field comprises: a capped bottle containing a premeasured quantity of a reagent reactable with hydrogen sulfide to form a precipitate; a second cap for the bottle, the second cap having mounted on at least a portion of its inner face a water-absorbent paper or fabric which serves as the substrate for the colorimetrically responsive reagent; an effervescent alkali metal bicarbonate tablet which is chargeable to the bottle; a second bottle containing the colorimetrically reactive reagent, said reagent bottle being normally closed, and means for transferring a portion of the colorimetrically responsive reagent to the water-absorbent substrate on the second cap.

17 Claims, 2 Drawing Figures

KIT AND METHOD FOR TESTING LIQUIDS FOR HYDROGEN SULFIDE CONTENT

BACKGROUND OF THE INVENTION

1. Field of the Invention

The invention relates to an analytical method for hydrogen sulfide and a kit for carrying out the method.

2. Description of the Prior Art

For various reasons, it is frequently desirable to know the amount of hydrogen sulfide present in a sample of liquid, and for this purpose, many laboratory techniques have been developed. See for example Marsh, U.S. Pat. No. 3,660,035, which teaches dispersing the $H_2S$ in a known quantity of a hydrocarbon into an ionic state and titrating with a standard cadmium salt solution to determine the hydrogen sulfide content of the hydrocarbon. Such laboratory techniques, however, are not easily adapted for field use, particularly by personnel who are untrained in analytical techniques. Various colorimetric $H_2S$ test kits are available, such as the Hach Model HS-6 and HS-7 kits (illustrated in Hach Catalog no. 11A, page 27), for field analysis of aqueous samples. These kits, however, are said to be useful for water samples, but use on oils or emulsions is not suggested. Also, quantitative measure ment is based on a visual evaluation of the degree or intensity of color change, so that results are not particularly accurate. Withair, *Chemistry and Industry*, Apr. 19, 1975, page 355 discloses that a portable chromatographic method and apparatus is used for measuring the amount of $H_2S$ in crude oil, but does not disclose the nature of the proprietary detector tube essential to practice the method. Moreover, the system of Withair is not useful on aqueous samples.

In some instances, it is necessary to know whether or not a sample contains $H_2S$ in excess of a certain preselected concentration. For example, in oil field operations in Texas, it is necessary to now whether fluids employed in well treatments have in excess of 100 milligrams per liter (mg/l) $H_2S$ to determine whether the provisions of Texas Railroad Commission Rule 36 apply. Since produced formation fluids—both aqueous, oil based, and emulsified fluids—are frequently reinjected as treating fluids, a single method is needed to quickly give an accurate analysis as to whether the preselected $H_2S$ concentration is exceeded, regardless of whether the sample is oil based, water based, or emulsified. Although the method must give an accurate indication as to whether the preselected concentration is exceeded, the method need not quantitatively indicate by how much the preselected concentration is exceeded or by how much the preselected concentration exceeds the actual concentration.

Also of interest is *Encyclopedia of Industrial Analysis*, Vol. 15, page 568, which teaches in conjunction with analyzing for mercaptans in hydrocarbons, that $H_2S$ should first be removed from the sample by precipitation using a solution of cadmium sulfate in sulfuric acid.

The teachings of each of the aforementioned patents are expressly incorporated herein.

SUMMARY OF THE INVENTION

One aspect of the present invention is a method for qualitatively determining whether or not a liquid contains hydrogen sulfide in excess of a preselected concentration. The principle of the method is to first remove from the liquid a stoichiometric quantity of the $H_2S$ equivalent to the quantity of $H_2S$ which would be present in a sample containing $H_2S$ in exactly the preselected concentration, and then determine whether any $H_2S$ remains in the liquid. This is accomplished by admixing a preselected quantity of the liquid to be tested with a metal cation capable of reacting with sulfide ion to form a precipitate. The quantity of metal cation provided is that which is stoichiometrically sufficient to react with the hydrogen sulfide which would be present in the preselected quantity of the liquid if the liquid contained hydrogen sulfide at the preselected concentration. After the metal cation has had time to react with the hydrogen sulfide if in fact any were initially present, the liquid is purged with an inert gas to remove unreacted hydrogen sulfide, if any, from the liquid. The gas which has contacted the liquid is permitted to be in fluid communication with, and thus contacts, a reagent which is colorimetrically and selectively responsive to hydrogen sulfide. Finally, the color of the colorimetrically responsive agent is observed. A color indicative of the presence of hydrogen sulfide indicates the initial sample had a hydrogen sulfide concentration in excess of the preselected concentration, whereas a color or lack of color change indicative of no hydrogen sulfide indicates the initial sample had a hydrogen sulfide concentration substantially equal to or less than the preselected concentration. The method may be used on aqueous fluids, oily fluids, or emulsified fluids, without pretreatment of the fluids.

Another aspect of the invention is a field kit containing the necessary means for carrying out the method. Broadly, the kit comprises:

(a) at least one reaction vial having an opening sealably closeable by a lid means and containing means for removing a quantity of hydrogen sulfide from a sample of liquid, said removal means comprising a preselected quantity of a reagent in aqueous solution, said reagent being reactable with hydrogen sulfide to form a precipitate;

(b) at least one first lid means sealably but removably closing said vial opening;

(c) at least one second lid means adaptable for sealably but removably closing the vial opening upon removal of the first lid means, said second lid having on at least a portion of its inner face—i.e., on that face in fluid communication with the interior of the vial when the lid sealably closes the vial—a water absorbent paper or fabric adapted to support an indicating means;

(d) at least one means for generating an inert gas, comprising at least one alkali metal bicarbonate tablet chargeable to the reaction vial via the vial opening upon removal of the first lid means;

(e) a reservoir vial having an opening and containing means for indicating the presence of hydrogen sulfide, said means comprising an aqueous solution of a reagent colorimetrically and selectively reactive with hydrogen sulfide, said opening being closed by means for closing said opening; and (f) means for transferring a portion of said indicating means from said reservoir vial to said water absorbent paper or fabric.

The kit essentially contains one of each of (a)–(f), but may contain a plurality of items (a) through (d) so that analyses may be performed on a plurality of samples.

FURTHER DESCRIPTION OF THE INVENTION

Figure 1:
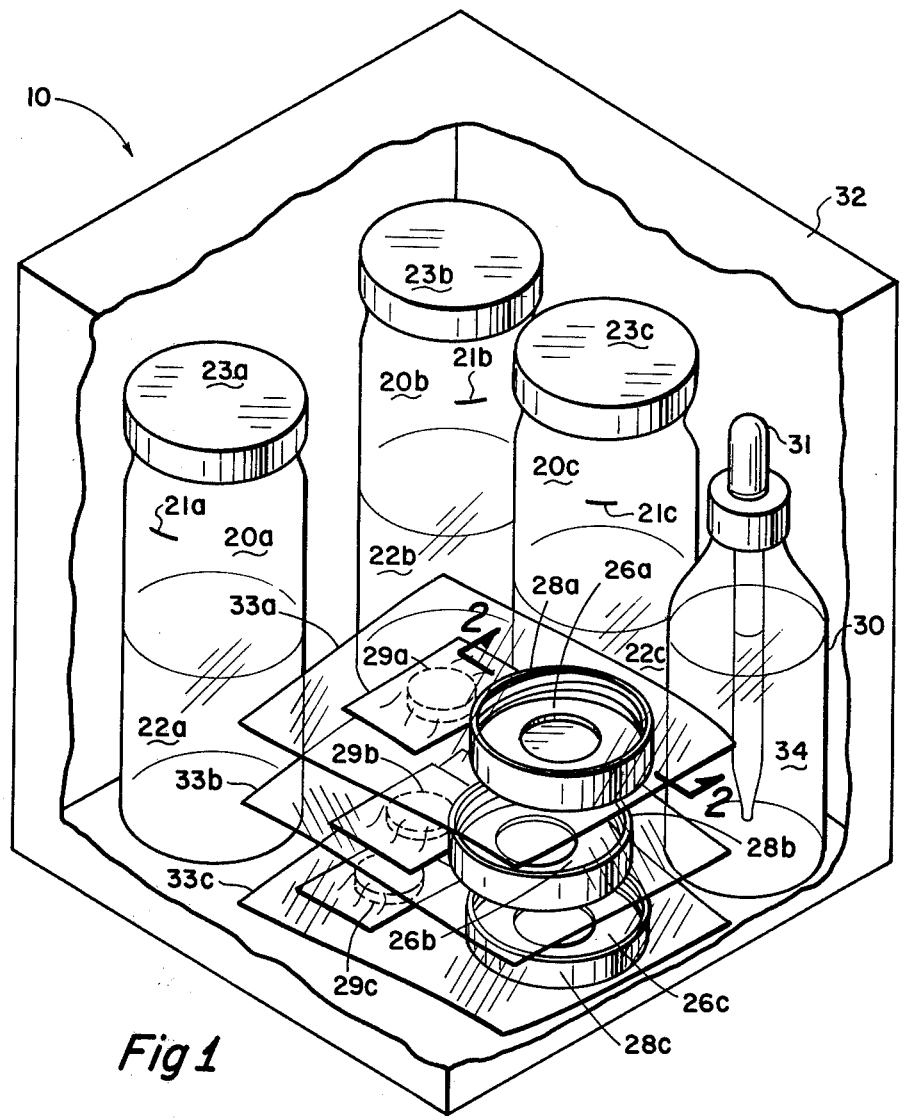
FIG. 1 is a view in perspective showing a kit according to the present invention.
Figure 2:
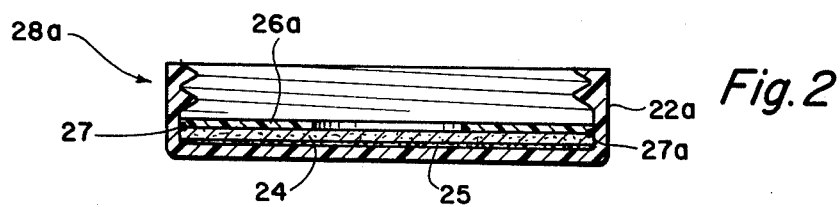
FIG. 2 is a cross sectional view along the line 2—2 in FIG. 1 showing the assembly of the second lid means.

In the precipitation step, any metal ion may be employed which will quantitatively precipitate sulfide ion from the liquid. Examples include $Zn^{(II)}$, $Fe^{(II)}$, $Hg^{(II)}$, $Ni^{(II)}$, $Pb^{(II)}$, $Sn^{(II)}$ and $Cd^{(II)}$. Preferably, a salt of one or more of the foregoing is dissolved in an aqueous solution and, if necessary, the pH is adjusted to a level at which the salt is readily soluble but at which the corresponding sulfide precipitates. Preferably, the precipitate-forming cation is provided as cadmium sulfate in an aqueous solution of sulfuric acid having a pH between about 3 and 7.

Arbitrarily selecting one of the quantity of fluid to be tested or the quantity of metal cation to be employed, one skilled in the art will be able to calculate the other quantity, depending on the preselected concentration of $H_2S$ which is of interest. In so doing, the quantity of metal cation employed should be substantially exactly that required to precipitate the $H_2S$ which would be present in a given quantity of the liquid having an $H_2S$ concentration equal to the preselected concentration. For example, if 100 mg/liter $H_2S$ is the preselected concentration and 25 ml is the quantity of fluid to be tested, 8.25 mg of $Cd^{(II)}$ is employed.

In carrying out the precipitation step, the liquid to be tested and the precipitating cation are brought into contact with one another sufficiently and for a sufficient time for a precipitate to form if any $H_2S$ is present at all. For example, the reaction vial may be shaken vigorously for about half a minute, and then permitted to stand for a minute or two.

Next, the liquid to be tested (and conveniently the entire reaction medium including any precipitate which may have formed) is purged with a substantially inert, $H_2S$-free gas such as nitrogen or carbon dioxide to remove any unreacted $H_2S$ from the liquid. Preferably, the inert gas is generated in situ. This may be conveniently done by adding an effervescent alkali metal bicarbonate tablet, such as an Alka-Seltzer brand effervescent tablet, to the reaction mixture.

After passing through the liquid the inert gas is brought into contact with a reagent which is colorimetrically and selectively responsive to the presence of hydrogen sulfide. Suitable reagents, for example, are aqueous solutions of soluble salts of $Pb^{(II)}$, $Cu^{(II)}$, or $Hg^{(II)}$, e.g. an approximately 20% lead acetate trihydrate solution. The concentration of the indicator solution is not critical, however. If desired, the gas may be passed through such an indicator solution. Preferably, however, an absorbent paper or fabric substrate, most preferably white in color, is moistened with the indicator solution and the gas is permitted to come into contact with the so treated substrate.

Finally, by observing whether or not a color change indicative of $H_2S$ has occurred, a determination is made as to whether or not the liquid initially contained $H_2S$ in an amount greater than the preselected concentration.

Referring to the drawings, a most preferred embodiment of the present invention will now be described in the context of a kit shown generally at 10, for determining whether or not a test liquid has an $H_2S$ concentration in excess of 100 mg/liter.

A series of 4-ounce laboratory bottles 20a, 20b, and 20c were calibrated with an indicator mark 21a, 21b, and 21c at the 50-ml volume level. To each was charged exactly 25 ml of a solution 22a, 22b, and 22c prepared by dissolving 0.753 g of $3CdSO_4.8H_2O$ in about 250 ml water in a 1 liter volumetric flask, adding 5 ml of 0.06 N sulfuric acid, and diluting to the mark with deionized water. Each bottle was then tightly closed with a threaded cap 23a, 23b, and 23c.

A piece of white filter paper 24 was mounted inside each of a series of caps 28a, 28b, and 28c having light colored lining 25 and also adapted to fit the above mentioned bottles. The paper was held in position by a flat annular plastic retainer 26a, 26b or 26c sized to fit snugly inside the cap. If desired, a small amount of adhesive 27, 27a may be used also. One each of the thusly prepared caps and a foil wrapped effervescent tablet 29a, 29b, and 29c were placed in protective plastic bags 33a, 33b, and 33c.

In a 2-ounce brown laboratory bottle 30 was dissolved 4 grams of lead acetate trihydrate in 20 ml of deionized water. The bottle was capped with a combination cap-glass dropper 31 which not only serves to cap the bottle, but also to transfer the lead acetate solution from the bottle to the filter paper lined lid 28a, 28b, or 28c when the test is carried out. Although it is convenient to have the dropper as an integral part of the cap, alternatively the dropper may be associated with the reagent bottle as a separate dropper provided in the kit. In another embodiment, the reagent bottle may be a squeezable plastic bottle having a capped nozzle for delivering the reagent.

Prior to use, the aforementioned components are conveniently stored or carried in a suitable protective container, such as a cardboard box 32, if desired.

In testing a sample of liquid, the cap 23a is removed from one of the jars containing the cadmium solution and 25 ml of the liquid to be tested is added to the bottle by charging liquid to the bottle until the fluid level reaches the 50 ml calibration 21a. The cap 23a is replaced and the bottle 20a is vigorously shaken by about 30 seconds. Next, one of the protective plastic bags 33a is opened, a drop of the lead acetate solution is placed on the paper 24 in one of the paper lined caps 28a and the foil is removed from the effervescent tablet 29a. When it appears that no additional precipitate is forming in the reaction bottle, in quick succession, the first cap 23a is removed, the effervescent tablet 29a is dropped into the reaction bottle 20a, and the bottle 20a is quickly closed with the second cap 28a lined with the paper 24 treated with indicator solution 34. When effervescence has ceased, the second cap is removed and the color of the treated paper 24 observed. A white to light tan coloration indicates the original sample contained no more than 100 mg $H_2S$ per liter of sample, whereas a dark brown to black color indicates an initial $H_2S$ concentration in excess of 100 mg/liter.

EXAMPLES

Except as noted, in each of the following examples, substantially the same equipment, procedures, and reagents just described in the description of the most preferred embodiment were employed. The concentration of the cadmium sulfate solution employed was such that each reagent test bottle contained sufficient cadmium to stoichiometrically precipitate the $H_2S$ from a 25 ml sample having an $H_2S$ concentration of 100.3 mg/liter.

EXAMPLE 1

A standard solution of $H_2S$ in Sol-Trol 100 brand high purity kerosene was prepared and titrated periodically using substantially the procedure set forth in *Universal Oil Products Laboratory Test Methods for Petroleum and its Products*, 4th Ed., page 173 (1959). Results were as follows:

| 11:05 a.m. | 289 mg $H_2S$/liter | }  |
|---|---|---|
| 11:15 a.m. | 277 mg $H_2S$/liter | } Ave. 282 mg/l |
| 12:05 a.m. | 241 mg $H_2S$/liter | |

EXAMPLE 2

Various quantities of the standard solution of Example 1 admixed with sufficient $H_2S$-free kerosene to make 25 ml were tested according to the method of the present invention. Results are shown in Table 1.

TABLE 1

| | | Kerosene Tests | | | |
|---|---|---|---|---|---|
| Run | $H_2S$ Standard soln.,ml | Clean Kerosene,ml | $H_2S$ Concentration[1],mg/ml Added | Excess | Paper Color |
| 1 | 8 | 17 | 90 | −10 | White |
| 2 | 10 | 15 | 113 | 13 | Black |
| 3 | 9 | 16 | 102 | 2 | Lt. Brown |
| 4 | 8.5 | 16.5 | 96 | −4 | White |

[1]$H_2S$ concentration in standard taken as 282 mg/l.
Work done 11:15–11:30 a.m. See Example 1.

Similar results are obtained when analyzing brines, crude oils, and the like. Occasionally, fluids are encountered containing surfactants which cause excessive foaming during the purge step. These fluids may be accommodated by simply using a larger reaction vial or by using a smaller quantity of alkali metal bicarbonate.

What is claimed is:

1. A method for qualitatively determining whether or not a liquid contains hydrogen sulfide in a concentration in excess of a preselected concentration, which comprises, in sequence:
    (a) admixing a preselected quantity of the liquid to be tested with a quantity of a metal cation capable of reacting with sulfide ion to form a precipitate, which quantity of cation is stoichiometrically sufficient to react with the hydrogen sulfide which would be present in said preselected quantity of liquid if said hydrogen sulfide were initially present at said preselected concentration;
    (b) purging the liquid with an inert gas to remove unreacted hydrogen sulfide from the liquid;
    (c) contacting a reagent colorimetrically and selectively responsive to the presence of hydrogen sulfide with the gas purged from the liquid;
    (d) observing the color of the colorimetrically responsive agent, a color change in response to hydrogen sulfide being indicative that the liquid tested contained hydrogen sulfide at a concentration in excess of said preselected concentration.

2. The method of claim 1 wherein said purging step includes generating said inert gas in situ.

3. The method of claim 1 wherein said colorimetrically responsive reagent is supported on a water-absorbent substrate.

4. The method of claim 1 wherein the colorimetric reagent contains $Pb^{(II)}$, $Cu^{(II)}$ or $Hg^{(II)}$.

5. The method of claim 4 wherein the colorimetric reagent is an aqueous solution of lead acetate.

6. The method of claim 1 wherein said inert gas is carbon dioxide.

7. The method of claim 6 wherein said carbon dioxide is generated in situ.

8. The method of claim 7 wherein said carbon dioxide is generated in situ by reacting at least one alkali metal bicarbonate with water in the reaction medium.

9. The method of claim 1 wherein the precipitate-forming cation is $Cd^{(II)}$, $Zn^{(II)}$, $Cu^{(II)}$, $Fe^{(II)}$, $Hg^{(II)}$, $Ni^{(II)}$, $Pb^{(II)}$, or $Sn^{(II)}$.

10. The method of claim 9 wherein the precipitate-forming cation is $Cd^{(II)}$.

11. The method of claim 10 wherein the $Cd^{(II)}$ is present as cadmium sulfate in an aqueous solution of sulfuric acid having a pH between about 3 and 7.

12. The method of claim 10 wherein the colorimetric reagent is lead acetate.

13. The method of claim 12 wherein the $Cd^{(II)}$ is present as cadmium sulfate in an aqueous solution of sulfuric acid having a pH between about 3 and 7, and wherein the inert gas is generated in situ by adding at least one alkali metal bicarbonate to the reaction medium.

14. The method of claim 13 which comprises:
    (a) adding the preselected volume of said liquid to be tested to a reaction vial having an opening adapted to be sealably closed by a lid and containing the cadmium sulfate solution;
    (b) closing the reaction vial and agitating its contents for a period of time sufficient to permit said cadmium to react with hydrogen sulfide which may be contained in said liquid;
    (c) in rapid succession, opening the vial, adding an alkali metal bicarbonate effervescent tablet to the vial, and reclosing the vial with a lid having mounted on its inner face, an absorbent paper or fabric moistened with an aqueous solution of lead acetate so that gas evolved from said liquid may contact said lead acetate treated paper;
    (d) upon cessation of effervescence, observing said paper for the appearance or absence of a dark brown or black color.

15. A test kit for qualitatively analyzing a sample of liquid to determine whether said liquid contains hydrogen sulfide in excess of a preselected concentration, which comprises:
    (a) at least one reaction vial having an opening sealably closeable by a lid means and containing means for removing a quantity of hydrogen sulfide from a sample of liquid, said removal means comprising a preselected stoichiometric quantity of reagent in aqueous solution said reagent being reactable with said preselected concentration of hydrogen sulfide to form a precipitate;
    (b) at least one first lid means sealably but removably closing said vial opening;
    (c) at least one second lid means adaptable for sealably but removably closing said vial opening upon removal of said first lid means, said second lid having an inner face in fluid communication with the interior of said vial when said lid sealably closes the vial, and, mounted on at least a portion of said inner face, a water-absorbent paper or fabric adapted to support an indicating means;

(d) at least one means for generating an inert gas, comprising an effervescent alkali metal bicarbonate tablet chargeable to said reaction vial via said opening upon removal of said first lid means;

(e) a reservoir vial having an opening and containing means for indicating the presence of hydrogen sulfide, said indicating means comprising an aqueous solution of a reagent colorimetrically and selectively reactive with hydrogen sulfide, said opening being normally closed by means for closing said opening; and (f) means for transferring a portion of said indicating means from said reservoir vial to said water-absorbent paper or fabric.

16. The kit of claim 15 wherein the reaction vial has at least one calibration to indicate a preselected volume within said vial.

17. The kit of claim 16 wherein said means for removing is an aqueous solution of cadmium sulfate having a pH between pH 3 and 7, said indicating means is an aqueous solution of lead acetate, and said means for closing and transferring is an eyedropper adapted to sealably close said reservoir vial.

* * * * *

UNITED STATES PATENT AND TRADEMARK OFFICE
CERTIFICATE OF CORRECTION

PATENT NO. : 4,174,202
DATED : Nov. 13, 1979
INVENTOR(S) : Benny E. Simpson

It is certified that error appears in the above-identified patent and that said Letters Patent are hereby corrected as shown below:

Col. 1, line 39, delete "now" and insert --know--.
Col. 3, line 11, after "$Zn^{(II)}$," insert --$Cu^{(II)}$,--.
Col. 4, line 44, delete "by" and insert --for--.
Col. 4, line 55, after "cap" insert --28a--.

Signed and Sealed this

Eleventh Day of March 1980

[SEAL]

Attest:

SIDNEY A. DIAMOND

Attesting Officer     Commissioner of Patents and Trademarks